United States Patent

Stream

[11] Patent Number: 5,831,727
[45] Date of Patent: Nov. 3, 1998

[54] BUBBLE ELIMINATION FROM LIQUID

[75] Inventor: Robert D. Stream, Loveland, Colo.

[73] Assignee: Hach Company, Loveland, Colo.

[21] Appl. No.: 848,697

[22] Filed: Apr. 29, 1997

[51] Int. Cl.[6] ............................. G01N 1/10; G01N 21/49
[52] U.S. Cl. .......................... 356/246; 356/440; 250/573
[58] Field of Search .................................. 250/573, 570; 356/440, 246

[56] References Cited

U.S. PATENT DOCUMENTS

| | | | |
|---|---|---|---|
| 3,560,099 | 2/1971 | Boe et al. ............................... | 356/410 |
| 3,867,042 | 2/1975 | Mayer et al. ........................... | 356/246 |
| 4,740,709 | 4/1988 | Leighton et al. ....................... | 356/246 |
| 5,601,727 | 2/1997 | Bormann et al. ....................... | 210/767 |

*Primary Examiner*—Frank G. Font
*Assistant Examiner*—Zandra V. Smith
*Attorney, Agent, or Firm*—Dean P. Edmundson

[57] ABSTRACT

Apparatus and a method are described for eliminating gas bubbles from a moving liquid stream. The apparatus includes a plurality of chambers having an open top. Each chamber directs the moving liquid stream upwardly through an area of reduced diameter and then downwardly to an opening into an adjacent chamber. The bubbles are thereby urged upwardly to the top of the liquid where they burst and are vented to the atmosphere. The apparatus and method are especially useful, for example, in a turbidimeter.

24 Claims, 11 Drawing Sheets

BUBBLE ELIMINATION FROM LIQUID

FIELD OF THE INVENTION

This invention relates to bubble elimination from a liquid. In a more particular aspect, this invention relates to elimination of air bubbles from a liquid such as water. In yet another aspect, this invention relates to turbidity sensors and particularly to a turbidity sensor which rapidly responds to a change of turbidity in a flow of fluid while eliminating the influence which bubbles have on the light-measuring characteristics of the sensor.

BACKGROUND OF THE INVENTION

Turbidity can be described as an expression of the optical properties that causes light to be scattered and absorbed rather than transmitted in straight lines through a fluid. Turbidity is generally interpreted by the layman as a measure of the relative clarity or purity of a liquid.

Devices for measuring turbidity in a process or flowing stream of fluid generally consist of a light source, a lens to focus the light, and a detector or sensor located at 90 degrees from the light beam. The detector records the light energy impinging on its surface from all of the light scattered by particles or solids suspended in the fluid. Very clear or pure (low turbidity) fluid has few or very small particles suspended in it. These types of devices are commonly used, for example, to monitor water at a municipal drinking water treatment plant, or in a manufacturing facility which requires ultra-pure water, or in a food process facility which would require a fluid of a specified clarity.

In the production of the foregoing types of fluids, the presence of bubbles causes various problems. Large and small (micro) bubbles are produced through the constant motion of the fluid, air leaks in the piping, and the addition of various purifying chemicals. A nephelometer or turbidimeter "sees" a bubble in the same manner as a particle, and thus bubbles may provide a false value in the sensor. Historically, nephelometers have either ignored bubbles completely, removed the effect electronically, or physically attempted to remove them before they can enter the light path.

Removal of the bubbles has generally been attempted in one of three different methods. In one method, the fluid enters a stilling chamber either at the top or near the bottom and slowly moves to the opposite end before proceeding to the light sensor area. This chamber may have a vertical or horizontal orientation with or without internal baffles to increase the time the fluid is contained. One example of a type of apparatus using this method is shown in U.S. Pat. No. 3,849,002. The flow rate is typically very low which allows the bubbles time to migrate to the surface where they burst and the resultant gas is vented to the atmosphere. Given enough time, the larger bubbles do reach the surface and are removed. However, the very small or "micro" bubbles have a small buoyant force and they remain suspended in the fluid and are transported into the light sensor area.

In a second method, the fluid enters a chamber which is exposed to a vacuum or is aspirated in some manner. The vacuum causes the bubbles to rise to the surface and burst. If the liquid is exposed to the vacuum for too short a length of time, this technique fails to remove the "micro" bubbles. Also, if the exposure time is too long, or if too much vacuum is used, this lowers the vapor pressure of the fluid and produces even more bubbles.

In a third method, the fluid enters a centrifuge which forces the suspended particles and "micro" bubbles to the outside, and the large bubbles with their large buoyant force migrate to the center and are vented to the atmosphere.

U.S. Pat. No. 1,552,259 describes a technique involving centrifugal forces induced in a liquid by a vortex to separate the liquid and the bubbles. The lighter bubbles are then vented out of the center of the device. The vortex is created by inclined openings in an orifice plate, or the vortex can be created by a device such as a turbine stator. Thus, this patent is a classic example of removing bubbles (and other light particles) by subjecting the fluid to a centrifuge.

U.S. Pat. No. 4,075,062 uses several methods to remove bubbles. Some bubbles are removed by a screen mesh at the inlet to a cylinder. Bubbles which are larger than the mesh are stopped by the screen. The smaller bubbles are permitted to rise to the surface by their upward/downward path through several cylinders. Any bubbles which are still in solution and are adhering to the windows are washed away by the high velocity flow of the liquid.

There are a number of disadvantages associated with the foregoing apparatus. If the screen at the inlet becomes clogged, then there is no liquid flow. Also, bubbles impacting a screen can break up into smaller bubbles and pass through the screen, or the bubbles can grow at the screen and eventually produce an air lock. Further, to sweep bubbles away from the window would require a very high liquid velocity.

U.S. Pat. No. 5,259,219 describes a bubble rejection method utilizing angled walls of a reservoir. Presumably the reservoir acts as a stilling chamber and larger bubbles can rise to the top over time. The smaller bubbles pass through the sensor in an upward flow and apparently do not produce any adverse effects. If the outlet of the reservoir is smaller than some of the bubbles, then there is a chance of an air lock in the reservoir. If the holes become plugged with debris, then there is no vent for the bubbles.

U.S. Pat. No. 5,331,177 describes apparatus in which bubbles are "discouraged" from passing in front of the light beam by protrusions on the side of the conduit. The bubbles that maintain contact with "inner cylindrical surface" find it easier to go around the protrusions (which contain the light beam) than over them.

The foregoing patent has no provision for removing bubbles from the fluid or accounting for bubbles entrained in the fluid away from the wall. The protrusions would force the bubbles in the fluid away from the wall toward the center of the conduit, thus into the light beam. Also, the protrusions would have to be very large and the fluid velocity very low to prevent the bubbles from going over the protrusions.

It is apparent from the above that there exists a need in the art for a nephelometer or turbidity sensor which is capable of rapidly providing bubbleless fluid to the light path area and which at least equals or betters the known measurement characteristics. It is the purpose of this invention to provide a method and apparatus for eliminating bubbles in fluid samples.

It is another object of this invention to provide a method and apparatus for eliminating bubbles in liquid which is continuously flowing.

It is yet another object to provide a method and apparatus for eliminating bubbles in a continuously flowing liquid through a closed turbidimeter instrument in a rapid fashion so as to prevent particles in fluid suspension from settling out of the suspension. It is a still further object to provide a light chamber shape (e.g., in a turbidimeter) which reduces the amount of stray light and reduces the potential for bubble growth on the walls of the chamber.

SUMMARY OF THE INVENTION

This invention provides solutions for several problems that currently exist in determining the turbidity value of a fluid. It removes both large and small bubbles entrained in a fluid in a rapid manner while retaining all particles in suspension, and it reduces the stray light and bubble growth in the light chamber by shaping the chamber to eliminate any reflected light from the light source away from any surface or wall. It also routes the high velocity fluid flow against the walls to cleanse the chamber of any bubbles.

In a preferred embodiment of this invention, fluid (e.g., water) enters upwardly into a cylindrical non-pressurized container and the fluid is split into at least two channels which progressively decrease in size until the fluid is forced through a small orifice which gives the fluid added velocity before reaching the water/air surface. This upward velocity propels the bubbles entrained in the fluid to the surface where they burst and are vented to the atmosphere. The two channels and orifices are sized and shaped to prevent a violent interaction of the flowing stream of fluid with the fluid/air surface which may introduce more bubbles into the flowing fluid. The fluid then flows downward and into another two channels and the bubble releasing process is repeated. This downward/upward flow is repeated multiple times before the fluid proceeds downward and then horizontally into the light chamber area of an instrument (e.g., a turbidimeter). Immediately before entering the light chamber area, the water flow is passed through another restricting orifice to increase the velocity and to direct the flow tangentially against the vertical walls of the light chamber. This high velocity flow prevents any bubble formation on the walls. The vertical walls of the light chamber area are tapered slightly to increase the light path length of any stray light which may impact the walls. The light chamber as viewed from the top is a combination of cylindrical and rectangular shapes and is sized to completely encompass the image of the light source after the light passes through the focusing lens of the instrument. The fluid flow continues upwardly past the light detector and then outwardly to a drain.

Other advantages and features of the method and apparatus of this invention will be apparent from the following detailed description and the accompanying drawings.

BRIEF DESCRIPTION OF THE DRAWINGS

The invention is described in more detail hereinafter with reference to the accompanying drawings wherein like reference characters refer to the same parts throughout the several views and in which.

DETAILED DESCRIPTION OF THE INVENTION

Figure 1:
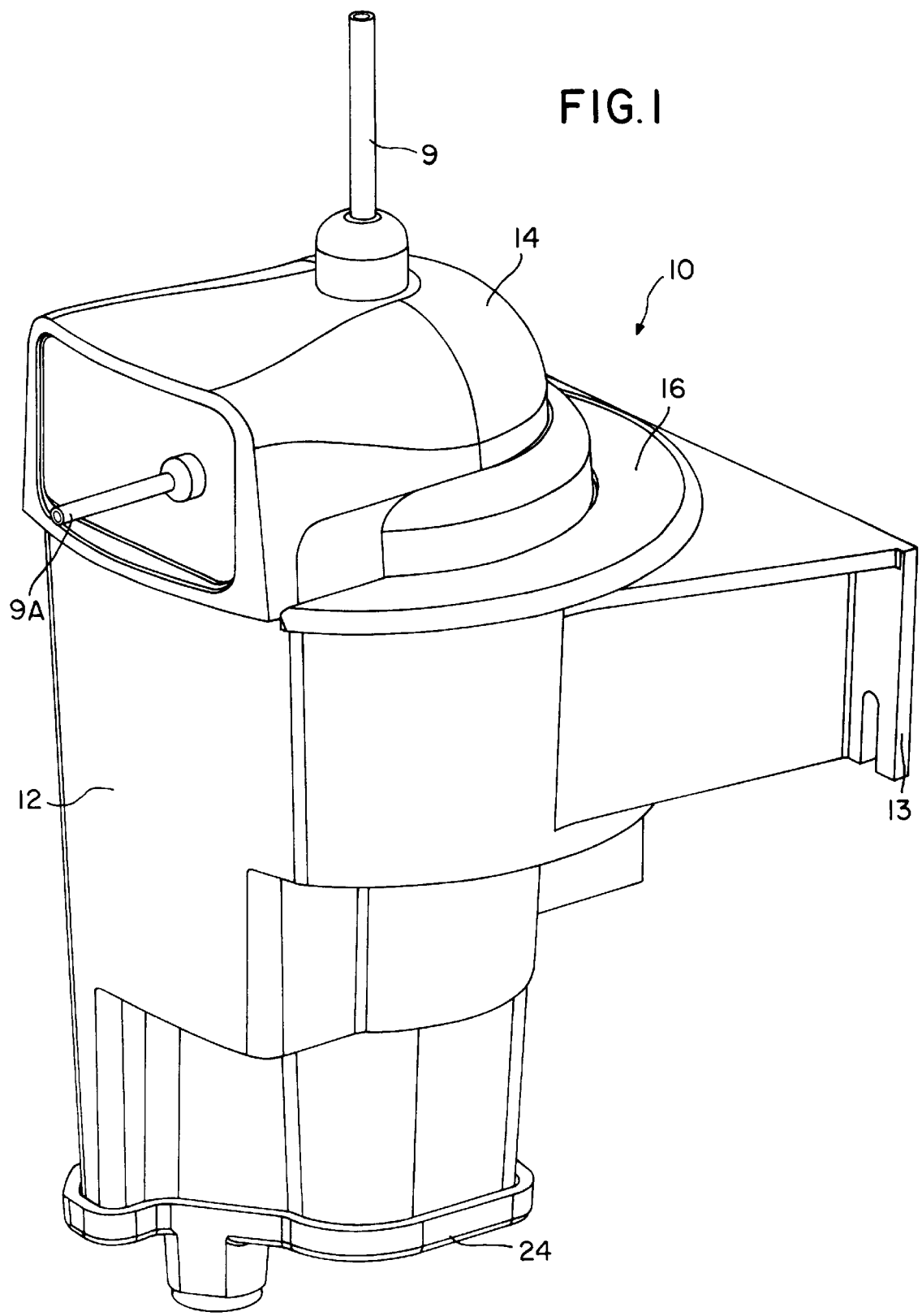
FIG. 1 is a front perspective view of a preferred embodiment of bubble elimination apparatus of this invention.

In the drawings there is shown a preferred embodiment of a turbidimeter apparatus 10 comprising an outer housing or enclosure 12 with a top cover 14. The housing 12 may include a mounting portion or bracket 13 which enables the housing to be secured or attached to a support (e.g., a wall). Cables 9 and 9A are for powering the light source and detector.

Figure 2:
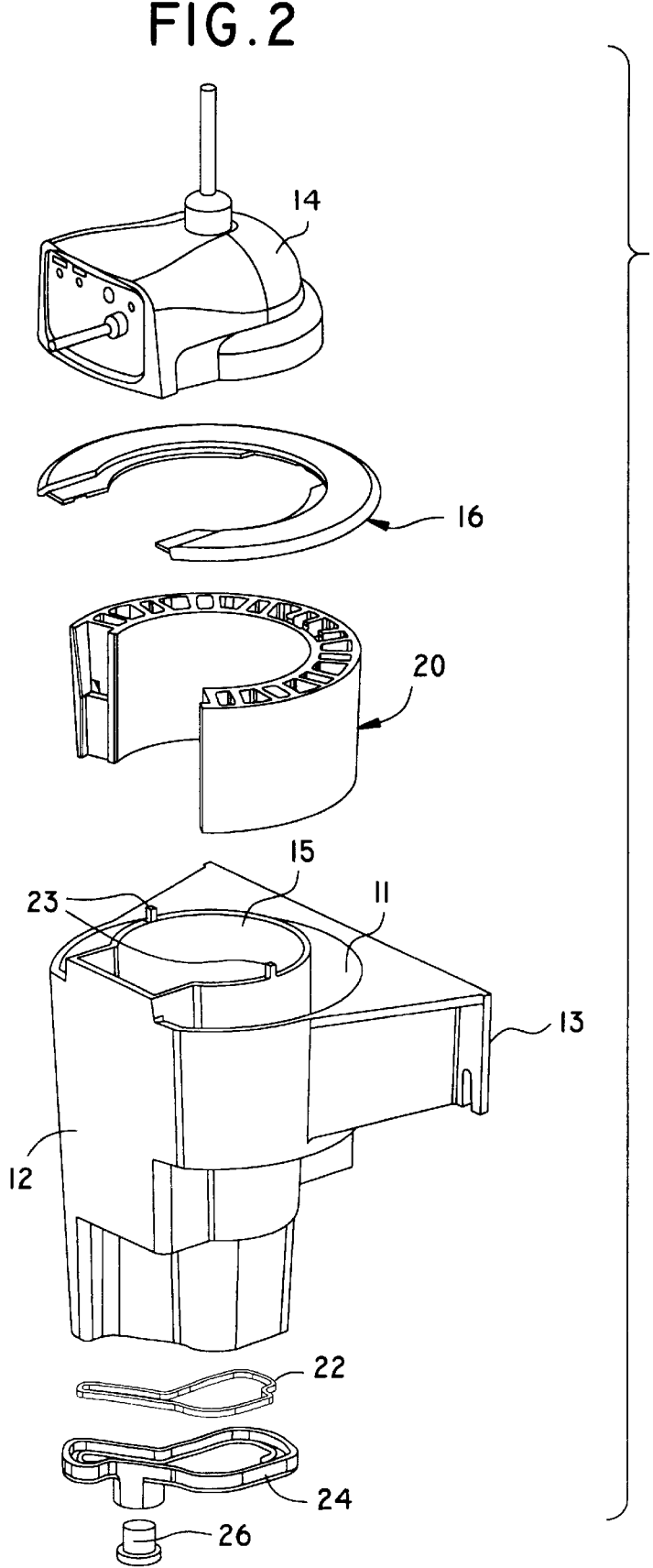
FIG. 2 is an exploded view of the apparatus shown in FIG. 1.

FIG. 2 is an exploded view of the apparatus of FIG. 1 showing covers 14 and 16, bubble elimination device 20, housing 12, gasket 22, bottom plate 24 and drain plug 26. The top of housing 12 includes alignment pins 23 for aligning top 14 with housing 12.

Within housing 12 is a compartment or cavity 11 which includes solid side walls, a floor with an inlet opening 11A and outlet opening 1B, and an open top. The cavity 11 is illustrated as being annular in shape, although the cavity may be any other desired shape.

Interiorly of annular cavity 11 is an open cavity 15. Cavity 15 is the location of the light source 30, lens 31, and detector 32. Below cavity 15 is cavity 17 which is a specially-shaped chamber which serves several functions. It provides a vertical path for the fluid to reach cavity 15, plus it is shaped to allow the light reflected from the light source to dissipate in the water before impacting a wall and reflecting back into the detector. Cavity 17 is tapered in the vertical direction to cause any stray light to reflect in an angular direction, thus taking a longer path before the stray light reaches the detector. The longer the path, the more the light energy is dissipated.

Positioned within cavity 11 is a bubble elimination device 20 which comprises a plurality of compartments or stages where flowing liquid (e.g., water) is forced upwardly through a narrow passage and then downwardly to the next stage where the process is repeated. There may be any desired number of these stages (e.g., 2 to 20, or more), depending upon the amount of bubbles in the liquid that are desired to be eliminated.

Figure 8:
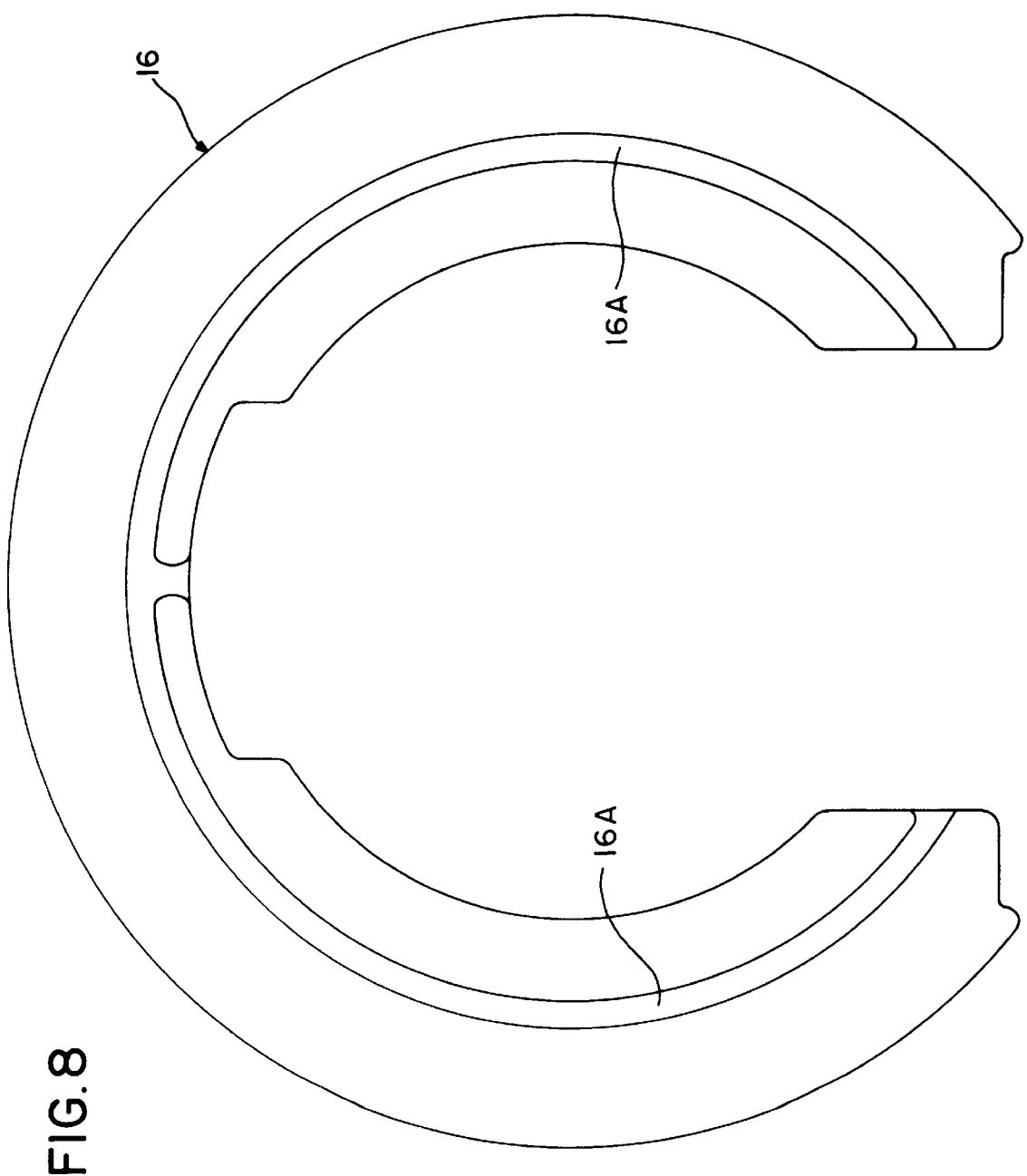
FIG. 8 is a bottom view of the cover which is positioned on top of the bubble elimination chamber or cavity.
Figure 9:
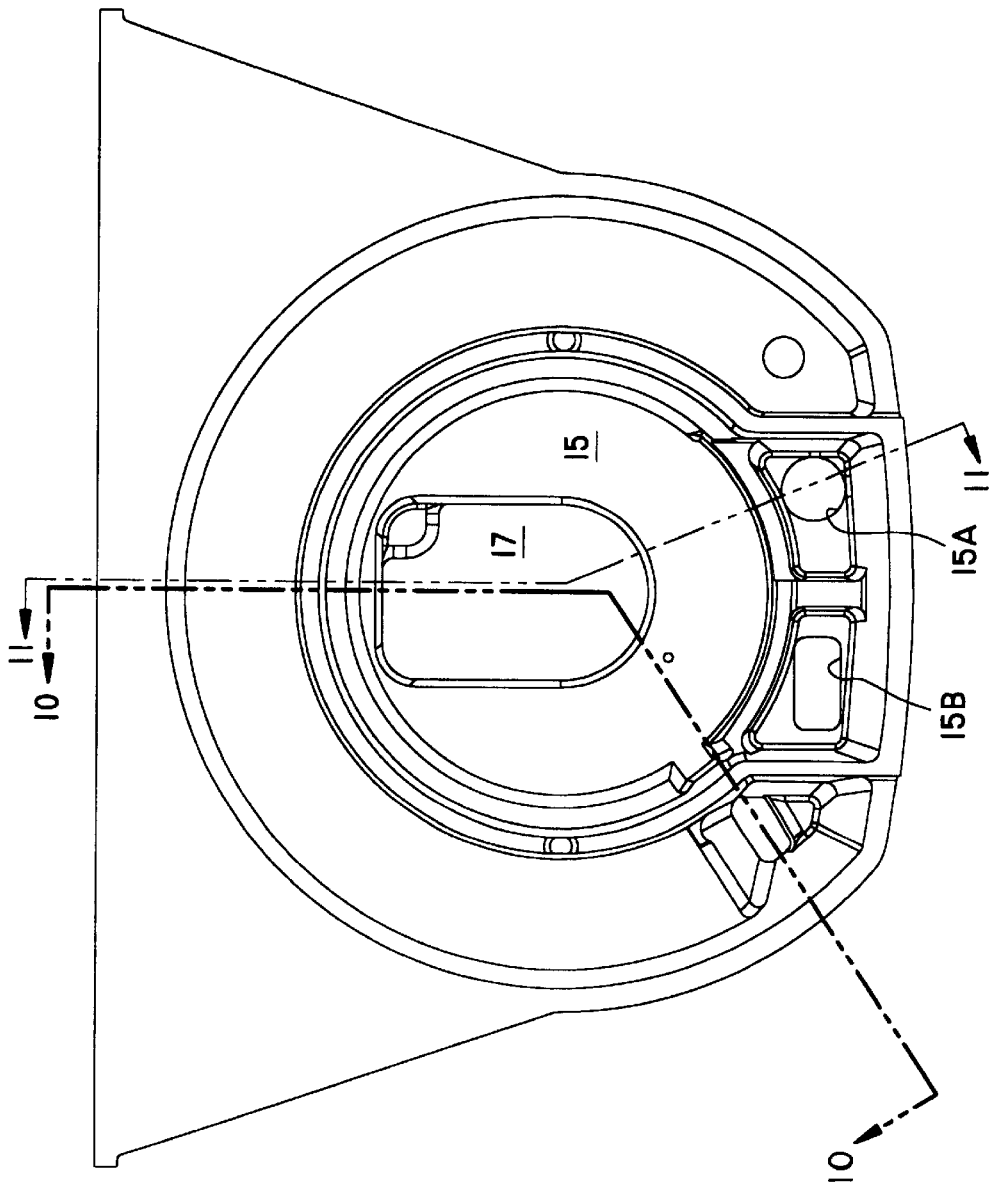
FIG. 9 is a top view of the apparatus of FIG. 1 without the covers and the bubble elimination device.
Figure 10:
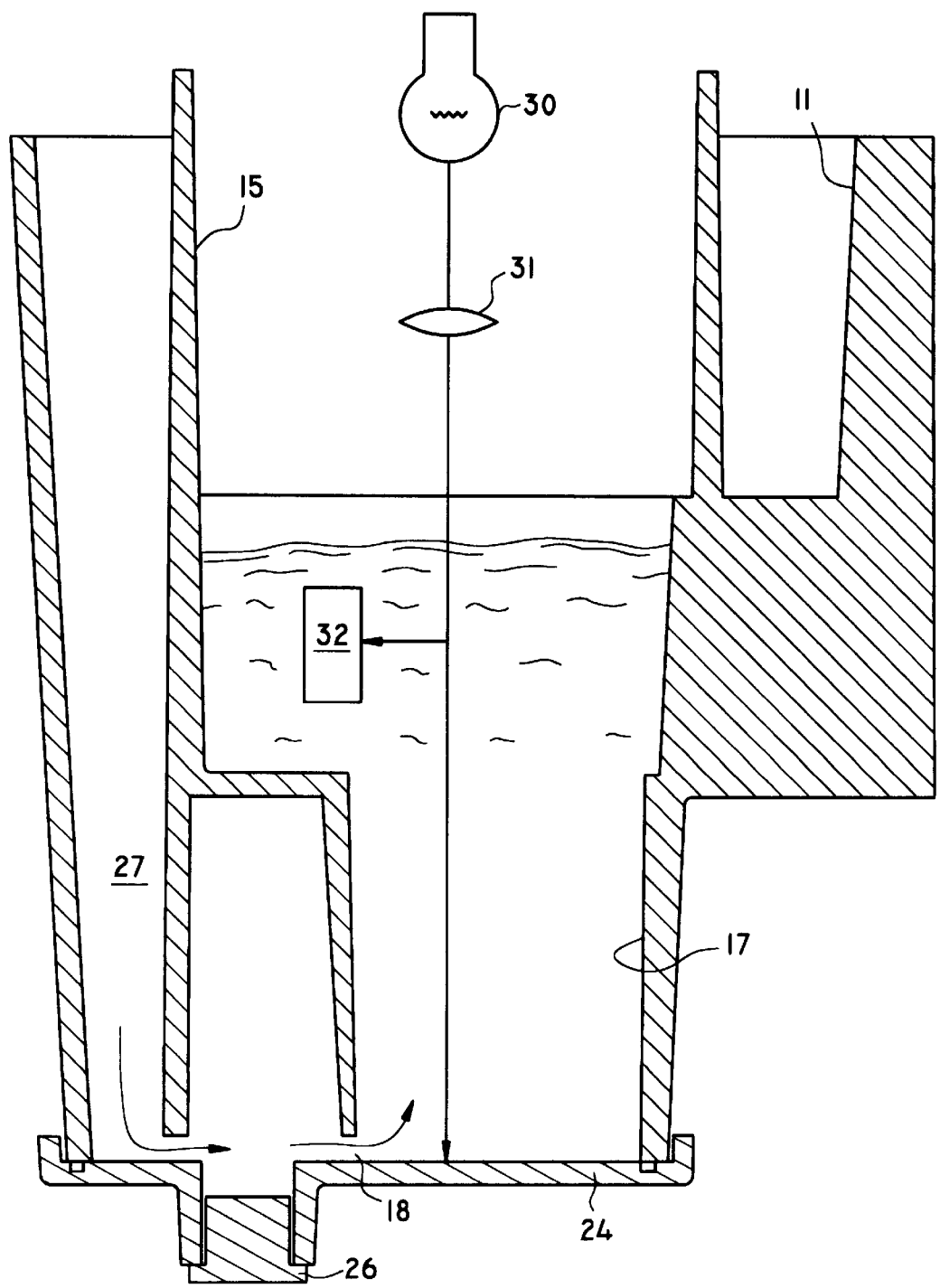
FIG. 10 is a cross-sectional view of the apparatus of FIG. 9 along 10—10.
Figure 11:
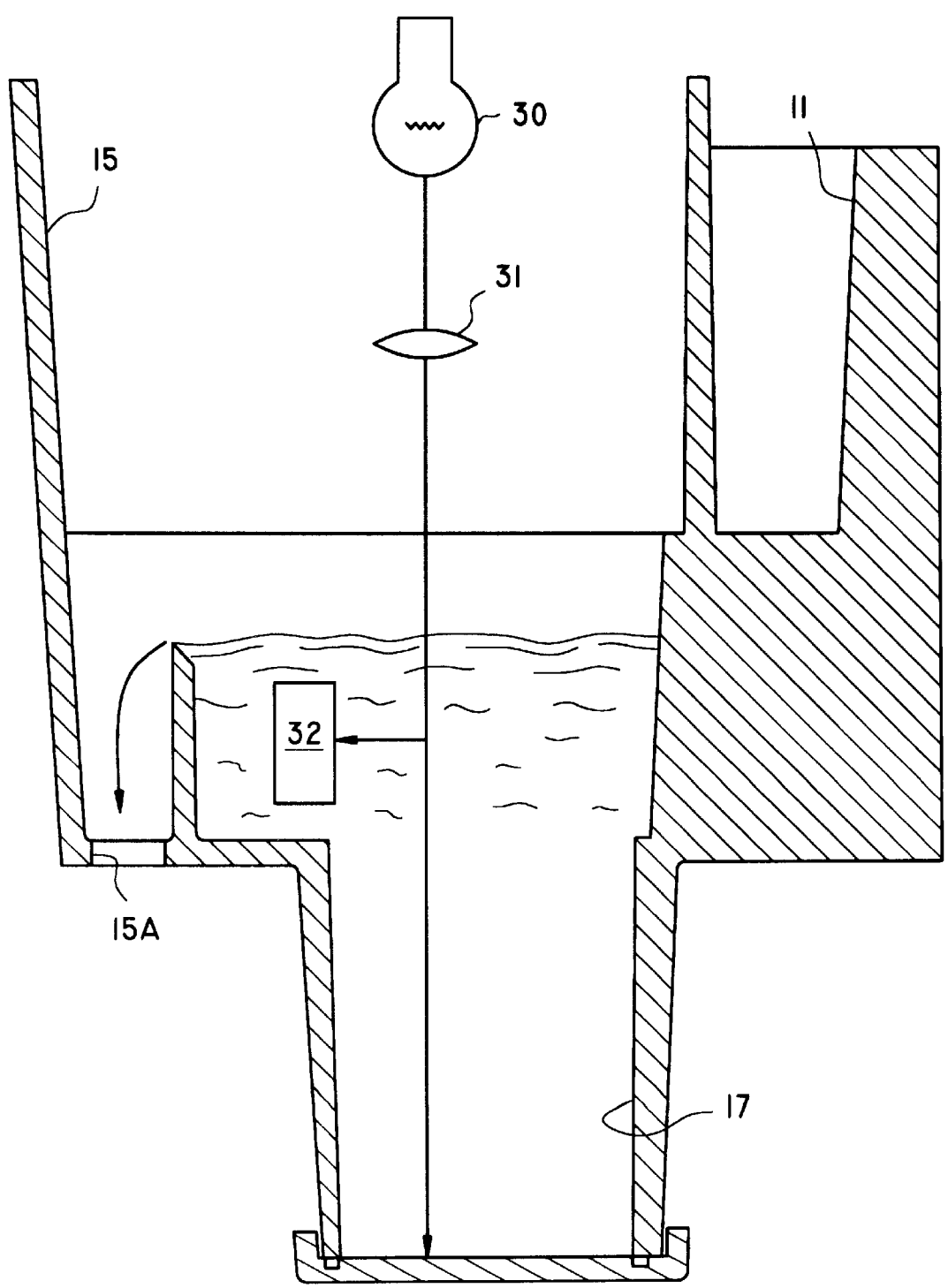
FIG. 11 is a cross-sectional view of the apparatus of FIG. 9 along line 11—11.

A cover 16 rests on top of the cavity 11. The underside of cover 16 (shown in FIG. 8) includes a groove or channel 16A which extends continuously along the length of the cover and is open to the atmosphere to enable air bubbles from the liquid in the cavity 11 to vent to the atmosphere. The width and depth of the groove or channel may vary, as desired.

Figure 3:
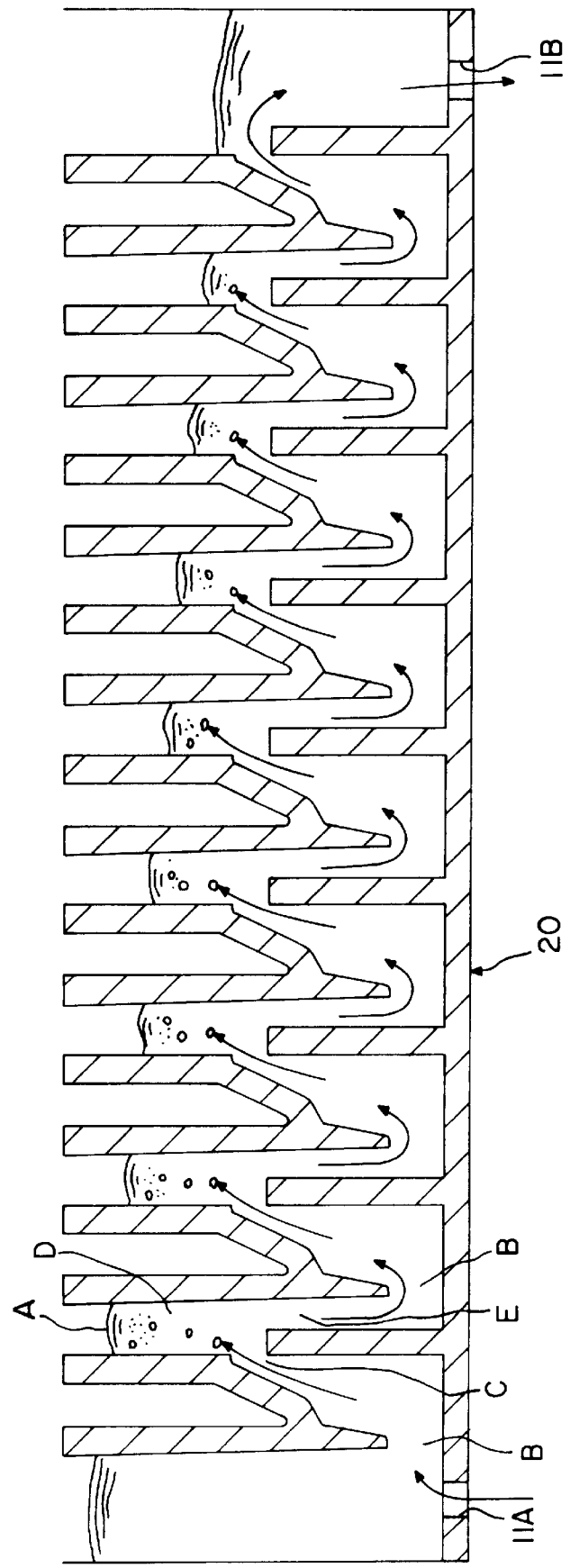
FIG. 3 is a cross-sectional view of a bubble elimination device of this invention.

FIG. 3 is a cross-sectional view illustrating the manner of operation of the bubble elimination device 20. Water enters inlet opening 11A in cavity 11 and flows through orifice B at low velocity and proceeds upward through a narrow orifice C (approximately 0.2×0.2 inch) at which point the velocity has increased due to the decreased area. The water/air mixture continues upward until contacting the air/water surface A where the bubbles burst. Then the water flows downward through chambers D and E and through orifice B of the next stage where the process in repeated. By virtue of the water passing through successive stages where it is forced upwardly through a narrow orifice and then downwardly again, any bubbles present in the incoming water are continually urged upwardly to the surface where they burst and are eliminated.

Due to the friction on the wall surfaces, the height of the air/water surface in each subsequent chamber is lower than the preceding surface. However, the velocity in each succeeding orifice C is less for the same reasons, but the relationship between the velocity at the orifice C and the height of the air/water surface is a constant. This relationship produces a gentle, rounded dome of water/bubbles at the air/water surface which allows the bubbles to release from the water. A different relationship, (higher flow, smaller orifice) produces a fountain effect at the air/water surface, thus producing more bubbles in the fluid. A lower flow rate or a larger orifice(c) does not allow the bubbles in the fluid to have enough energy to rise to the air/water surface, thus staying entrained in the fluid.

At a given flow rate the size of chamber D is important because (a) if the chamber is too small it can produce a fountain effect (where incoming water is forced upwardly and breaks through the air/water surface), and (b) if the chamber is too large it prevents the desired dome from forming at the air/water surface.

The size of orifices B and C is also important because if they are too small they restrict water flow, thus raising the height of the air/water surface and thereby preventing bubbles from reaching the surface before being flushed through to the next chamber. If either orifice B or C is too large, then the height of the air/water surface is lowered. As a result, there is a greater likelihood of the flowing water producing a fountain effect.

Experimental data suggests that with a water flow rate of 250 to 750 mL per minute, the size of each opening C should be 0.04 square inch when each opening B is 0.10 square inch and the total opening at E is 0.20 square inch and the total opening at D is 0.48 square inch. Another way of stating it is that if the opening at C is X square inches, then the opening at B is equal to 2.5x square inches, the opening at E is equal to 5.0x square inches, and the opening at D is equal to 12x square inches.

Figure 4:
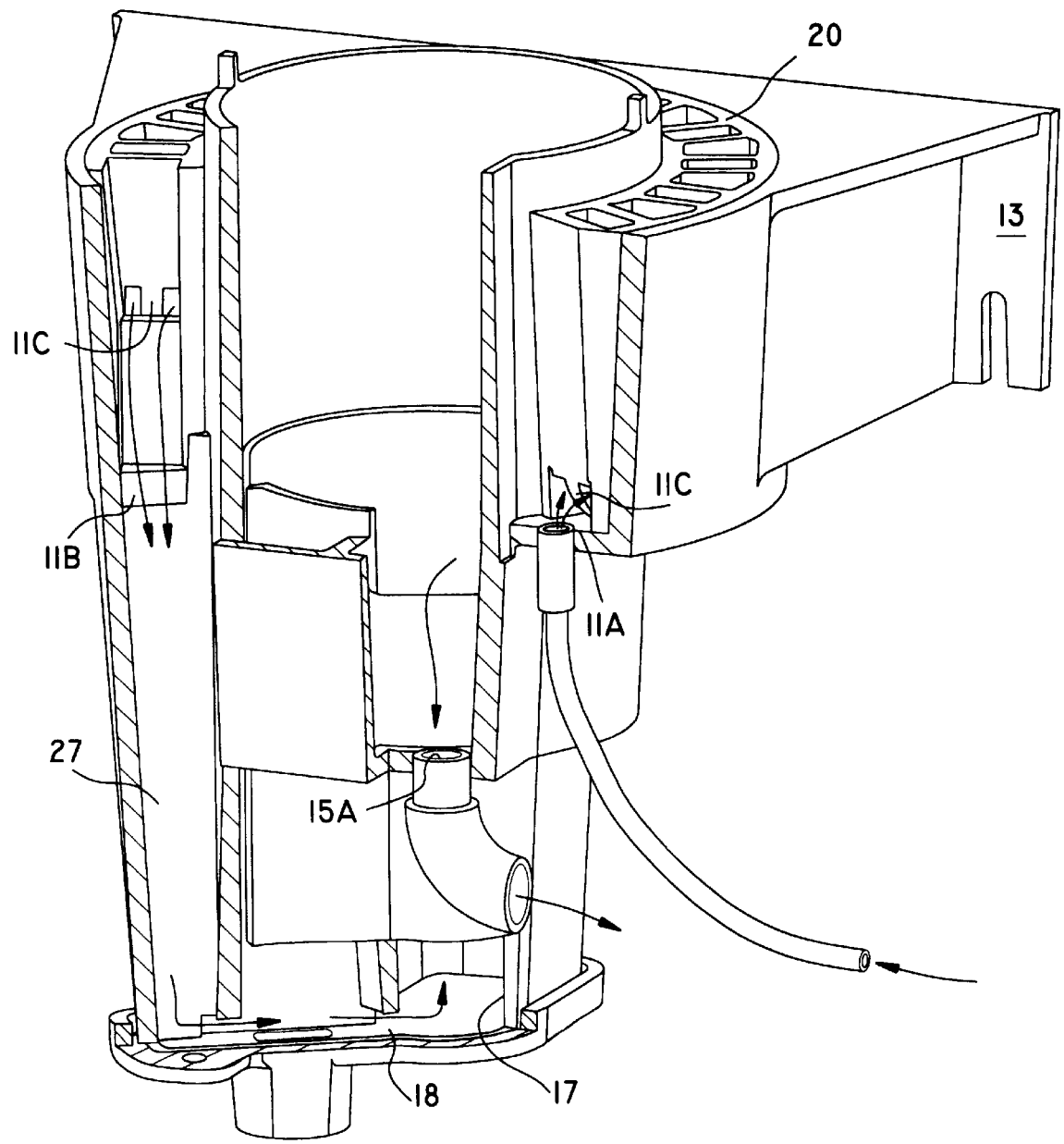
FIG. 4 is a side elevational, partially cut-away, view of the apparatus of FIG. 1.

FIG. 4 is a partially cut-away view showing where incoming water enters the bubble elimination device 20 through inlet opening 11A. Water which has passed through the device 20 exits at 11B and proceeds downwardly through passage 27, then horizontally across the floor of the housing through orifice 18 (which due to its reduced area increases the velocity of the water). Also, due to the angular placement of orifice 18 relative to cavity 17, this orifice directs the flow of water along the floor and vertical walls of cavity 17. This high velocity flow prevents particles and bubbles from accumulating in cavity 17.

The water then fills cavity 17 and exits through the outlet 15A. A light detector 32 is positioned in cavity 15 for detecting light which is scattered at 90° from the path of the light beam from light source 30 and lens 31. If the water level in cavity 15 reaches a very high level, then it may spill over and exit through drain overflow outlet 15B.

Figure 5:
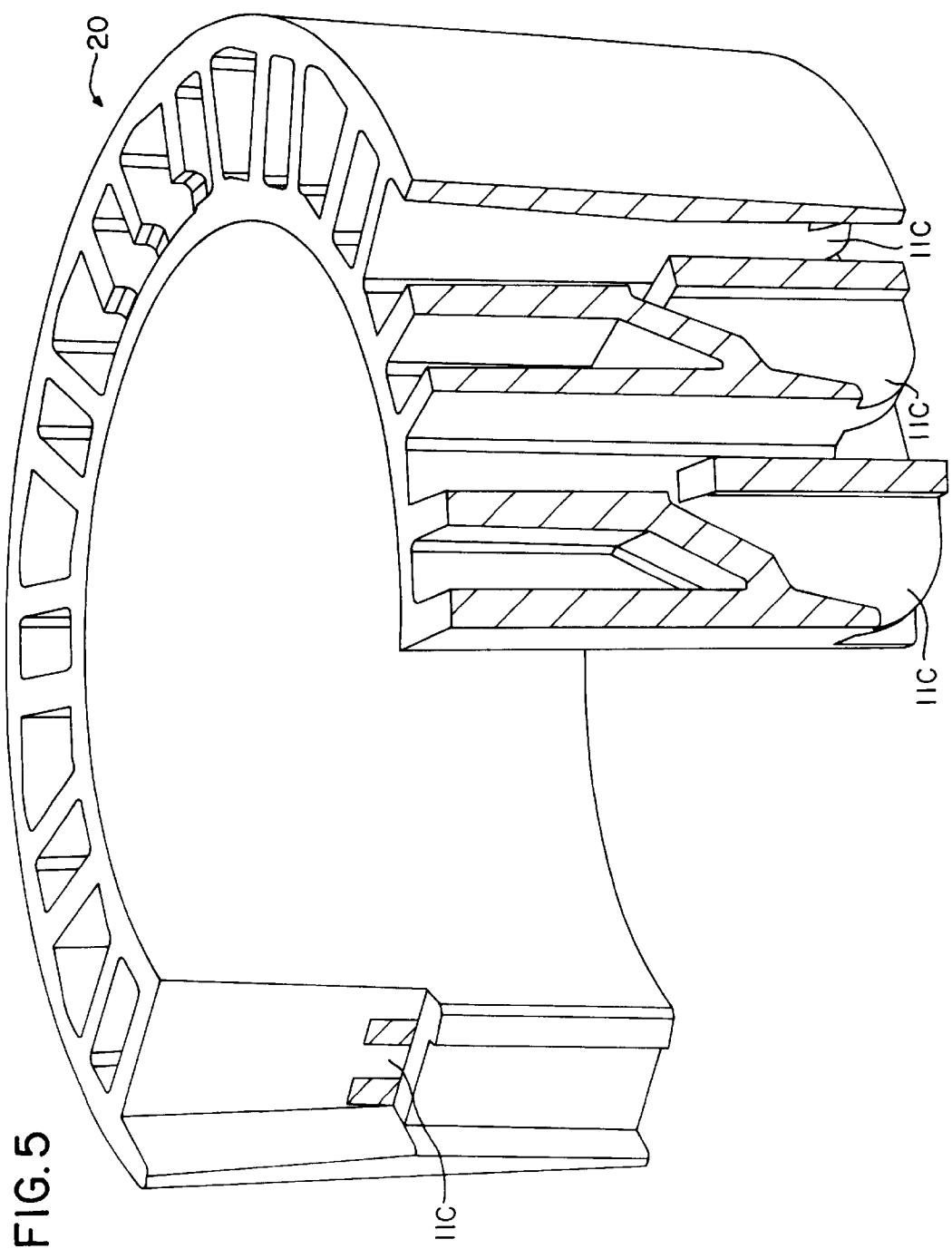
FIG. 5 is a perspective cut-away view of a preferred embodiment of bubble eliminating device of the invention.
Figure 6:
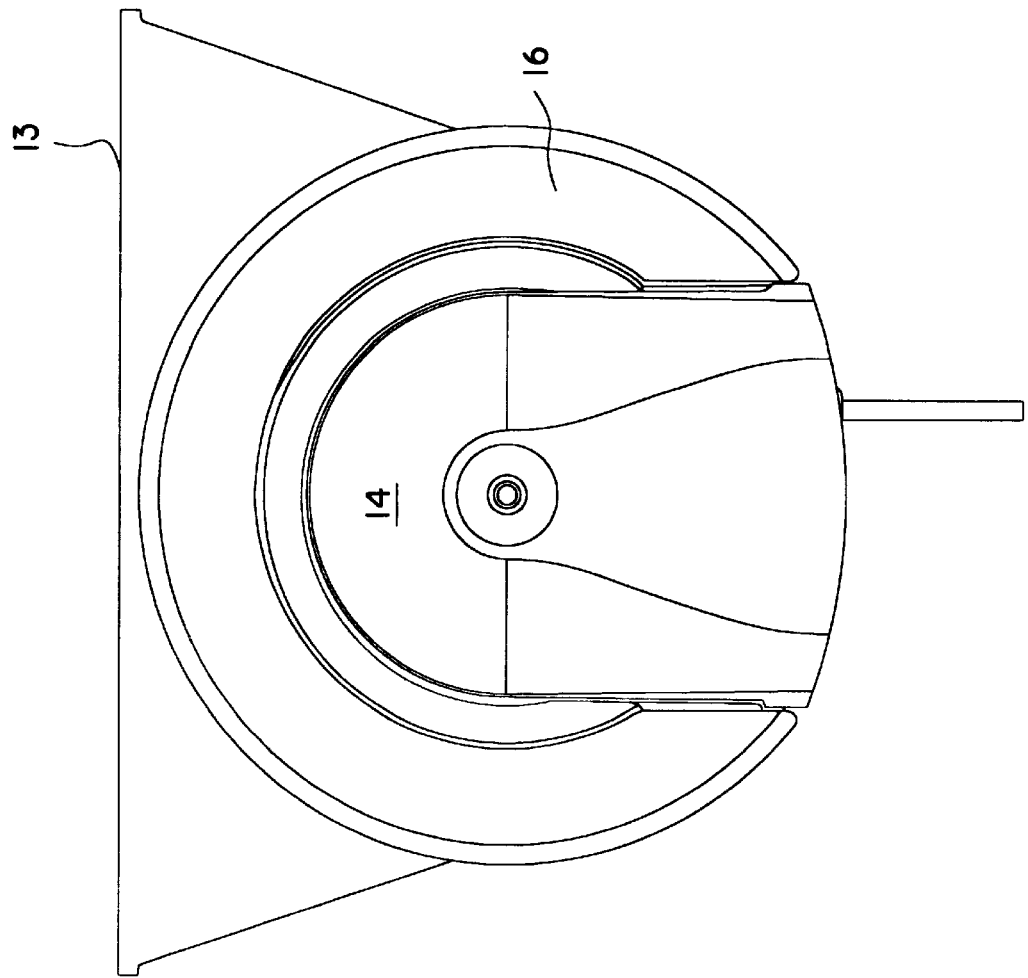
FIG. 6 is a top view of the apparatus of FIG. 1.
Figure 7:
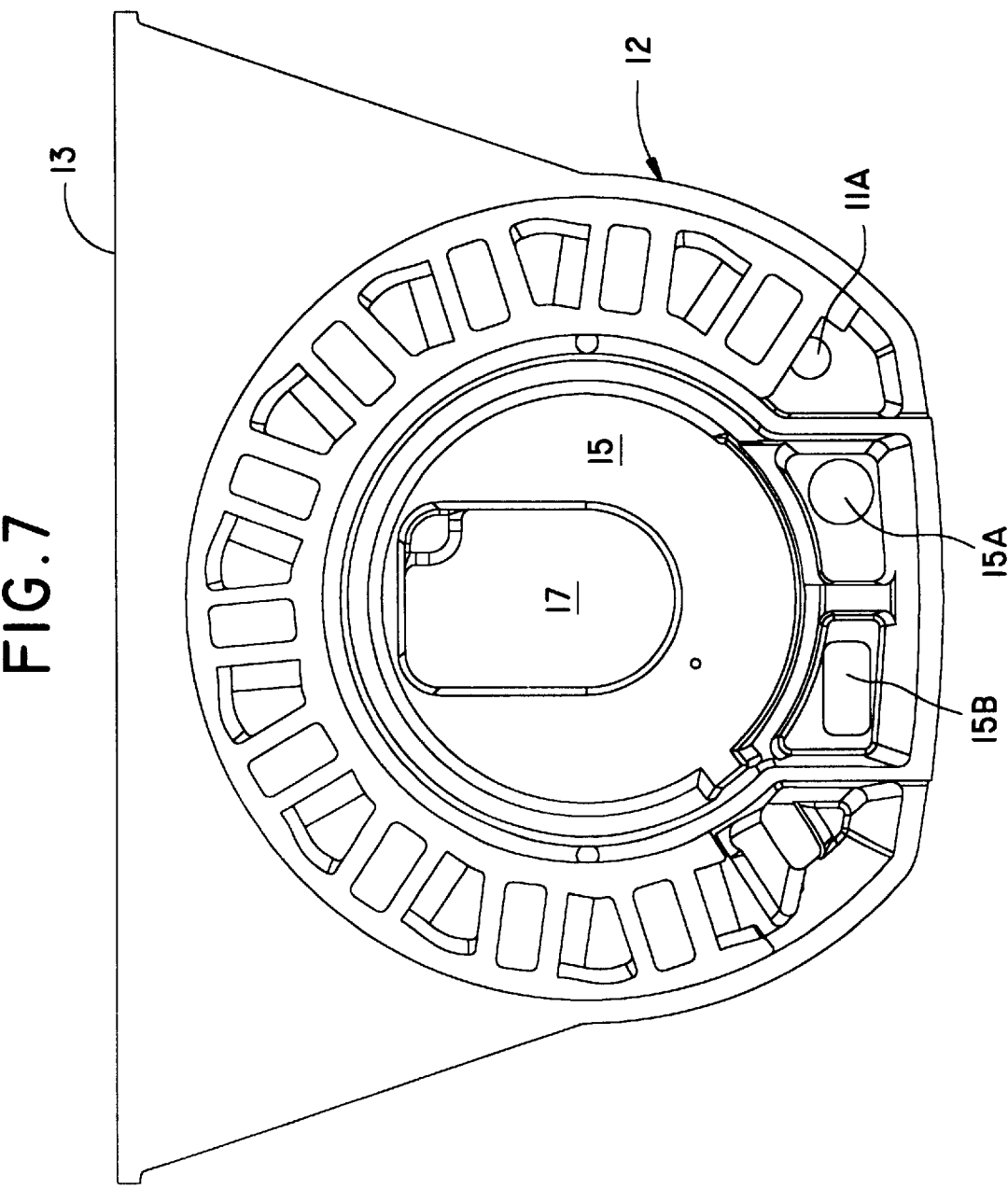
FIG. 7 is a top view of the apparatus of FIG. 1 without the covers.

The bubble elimination device 20 is very effective in removing bubbles from a moving stream of liquid (e.g., water). The device can be made in any desired shape, e.g., the annular body shape shown in FIG. 5, or it could be entirely linear, etc., so long as there are multiple chambers or stages where the flowing water stream proceeds upwardly through an orifice of reduced diameter and then proceeds downwardly through an orifice of greater diameter before repeating the processing in the next chamber or stage of the device. The upper end or top of each chamber is open to the atmosphere so that bubbles in the water can move to the air/water surface, as illustrated in FIG. 3. There may be as many successive chambers as desired in a single bubble elimination.

Another way to produce multiple chambers in a single device is to place one or more vertical walls interiorly of the device so as to form two or more chambers in side-by-side relationship for each stage. Such a wall is illustrated as wall 11C in FIG. 4 and 5.

Of course, another way to increase the bubble elimination effect is to connect two or more bubble elimination devices in series so that the flowing water must pass through all of the devices. The greater the number of chambers the water must pass through, the greater is the opportunity for bubbles to rise to the air/water surface and become eliminated.

Other variants are possible without departing from the scope of the present invention. The bubble elimination device is useful in any situation where it is necessary to remove bubbles from a liquid.

Although in the bubble elimination device shown in FIG. 3 the inlet 11A is in the floor of the device, it is also possible for the inlet to be above the floor (e.g. in a side or end wall or even at the top of the first chamber). Such a variation is considered to be equivalent to the device shown in FIG. 3. What is important is that the water flows more rapidly through an upper orifice of reduced diameter and then more slowly through a larger opening to a successive chamber where the process is repeated. This movement of the water allows the bubbles to move upwardly to the air/water surface in the manner shown in the drawings. The more times the process is repeated, the more bubbles are released.

What is claimed is:

1. Apparatus for eliminating gas bubbles from a moving liquid stream comprising a plurality of chambers having an open top and being adapted to direct said moving liquid stream upwardly through an area of reduced diameter and then downwardly to an opening into an adjacent chamber.

2. Apparatus in accordance with claim 1, wherein said apparatus includes an inlet end and an outlet end.

3. Apparatus in accordance with claim 2, further comprising a housing having upright side walls and a floor defining a cavity; wherein said chambers are positioned in said cavity.

4. Apparatus in accordance with claim 3, wherein said cavity is annular in shape.

5. Apparatus in accordance with claim 1, wherein there are at least eight of said chambers.

6. Apparatus in accordance with claim 1, wherein said chambers are integrally connected.

7. Apparatus in accordance with claim 1, wherein each said chamber is defined by (a) a floor, (b) a first upright wall member extending from said open top downwardly to a point above said floor and defining a first orifice between said floor and said first wall member, and (c) a second upright wall member extending upwardly from said floor and having an upper end; wherein a second orifice is defined between said upper end of said second wall and said first wall member; wherein said second orifice is smaller than said first orifice.

8. Apparatus in accordance with claim 7, wherein said first wall member includes a sloping surface extending upwardly to said second orifice.

9. Apparatus in accordance with claim 7, wherein the size ratio of said first orifice to said second orifice is in the range of about 2–3:1.

10. Apparatus in accordance with claim 1, further comprising a vertical wall splitting each chamber into two side-by-side sections.

11. In a turbidimeter of the type including a light source, sample cell, light detector, and a connection to a stream of liquid, an improvement which comprises apparatus for eliminating gas bubbles from said stream, wherein said apparatus comprises a plurality of chambers having an open top and being adapted to direct said stream of liquid upwardly through an area of reduced diameter and then downwardly to an opening into an adjacent chamber.

12. Apparatus in accordance with claim 11, wherein said apparatus includes an inlet end and an outlet end.

13. Apparatus in accordance with claim 12, further comprising a housing having upright side walls and a floor defining a cavity; wherein said chambers are positioned in said cavity.

14. Apparatus in accordance with claim 13, wherein said cavity is annular in shape.

15. Apparatus in accordance with claim 12, wherein there are at least eight of said chambers.

16. Apparatus in accordance with claim 11, wherein said chambers are integrally connected.

17. Apparatus in accordance with claim 11, wherein each said chamber is defined by (a) a floor, (b) a first upright wall member extending from said open top downwardly to a point above said floor and defining a first orifice between said floor and said first wall member, and (c) a second upright wall member extending upwardly from said floor and having an upper end; wherein a second orifice is defined between said upper end of said second wall and said first wall member; wherein said second orifice is smaller than said first orifice.

18. Apparatus in accordance with claim 17, wherein said first wall member includes a sloping surface extending upwardly to said second orifice.

19. Apparatus in accordance with claim 17, wherein the size ratio of said first orifice to said second orifice is in the range of about 2–3:1.

20. Apparatus in accordance with claim 11, further comprising a vertical wall splitting each chamber into two side-by-side sections.

21. Apparatus in accordance with claim 11, further comprising a main housing including first cavity in which said bubble elimination device is disposed and further including a second cavity in which said light detector is disposed.

22. Apparatus in accordance with claim 21, further including conduit means enabling water exiting said bubble elimination device to enter said second cavity.

23. Apparatus in accordance with claim 21, further comprising a cover member covering said bubble elimination device, wherein said cover member includes a channel to enable air to pass from the top of said chamber to the atmosphere.

24. A method for removing bubbles from a moving stream of liquid, the method comprising passing said stream through a device having a plurality of chambers each having a floor, side walls and an open top, wherein each chamber includes an inlet orifice and an outlet orifice, wherein said outlet orifice is above said inlet orifice and is smaller than said inlet orifice.

* * * * *